US012606688B2

(12) United States Patent
Nicolas et al.

(10) Patent No.: US 12,606,688 B2
(45) Date of Patent: Apr. 21, 2026

(54) METHOD FOR DEPOSITING NANO-OBJECTS ON THE SURFACE OF A POLYMER GEL COMPRISING ZONES WITH DISTINCT RIGIDITIES

(71) Applicants: Centre national de la recherche scientifique, Paris (FR); UNIVERSITE GRENOBLE ALPES, Saint Martin d'Heres (FR); Commissariat à l'énergie atomique et aux énergies alternatives, Paris (FR)

(72) Inventors: Alice Nicolas, Grenoble Cedex (FR); Camille Migdal, Grenoble Cedex (FR); Eline Lopez Soler, Grenoble Cedex (FR)

(73) Assignees: CENTRE NATIONAL DE LA RECHERCHE SCIENTIFIQUE, Paris (FR); UNIVERSITE GRENOBLE ALPES, Saint Martin d'Heres (FR); COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 1056 days.

(21) Appl. No.: 16/977,520

(22) PCT Filed: Feb. 27, 2019

(86) PCT No.: PCT/EP2019/054859
§ 371 (c)(1),
(2) Date: Sep. 2, 2020

(87) PCT Pub. No.: WO2019/166487
PCT Pub. Date: Sep. 6, 2019

(65) Prior Publication Data
US 2021/0002450 A1 Jan. 7, 2021

(30) Foreign Application Priority Data
Mar. 2, 2018 (FR) ...................................... 18 51833

(51) Int. Cl.
| | |
|---|---|
| *C08J 9/36* | (2006.01) |
| *C08J 3/075* | (2006.01) |
| *C08J 7/043* | (2020.01) |
| *C12N 11/087* | (2020.01) |
| *C12N 11/098* | (2020.01) |
| *G01N 15/14* | (2006.01) |
| *B82Y 30/00* | (2011.01) |

(52) U.S. Cl.
CPC ................ *C08J 9/36* (2013.01); *C08J 3/075* (2013.01); *C08J 7/043* (2020.01); *C12N 11/087* (2020.01); *C12N 11/098* (2020.01); *G01N 15/1484* (2013.01); *B82Y 30/00* (2013.01); *C08J 2205/022* (2013.01); *C08J 2301/00* (2013.01); *C08J 2329/04* (2013.01);

*C08J 2333/10* (2013.01); *C08J 2333/26* (2013.01); *C08J 2383/04* (2013.01)

(58) Field of Classification Search
CPC .......................................................... C08J 9/36
See application file for complete search history.

(56) References Cited

U.S. PATENT DOCUMENTS

| | | | |
|---|---|---|---|
| 6,881,448 B1* | 4/2005 | Hattori | ................... B05D 3/107 |
| | | | 427/202 |
| 9,758,598 B2 | 9/2017 | Gulino et al. | |
| 2002/0150723 A1* | 10/2002 | Oles | ......................... B05D 5/08 |
| | | | 264/340 |
| 2010/0068461 A1* | 3/2010 | Wallace | .............. B81C 1/00111 |
| | | | 428/156 |

(Continued)

OTHER PUBLICATIONS

Choi et al, Key Engineering Materials, 342-343, 2007, pp. 717-720 (Year: 2007).*

(Continued)

*Primary Examiner* — Irina Krylova
(74) *Attorney, Agent, or Firm* — B. Aaron Schulman, Esq.; Stites & Harbison, PLLC

(57) ABSTRACT

The invention concerns a method for depositing nano-objects on the surface of a gel comprising a polymer matrix having at least two contiguous zones of distinct rigidities, said method comprising the steps of:

Figure 1:
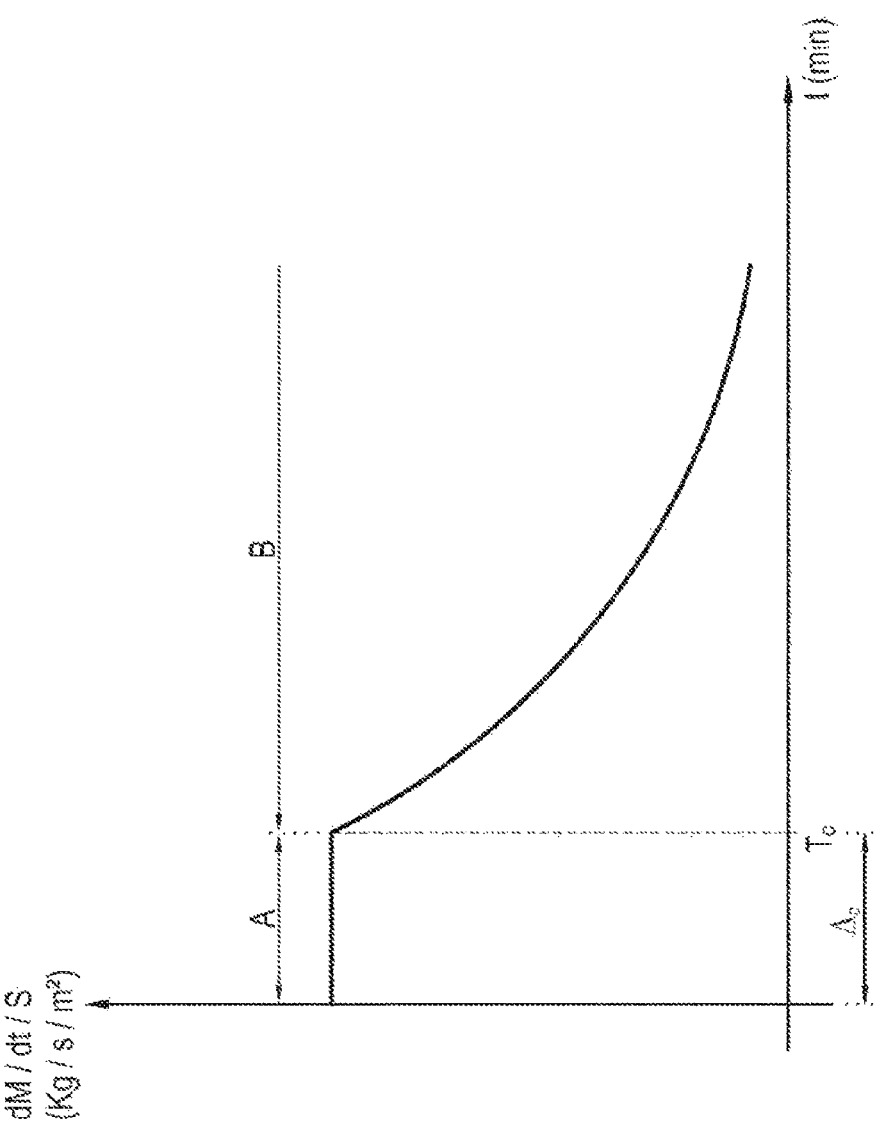

a) providing a gel comprising a polymer matrix and a solvent within the polymer matrix, the polymer matrix forming a three-dimensional array capable of swelling in the presence of said solvent, wherein the solubility of the polymer matrix, at 1 bar and 25° C., in the solvent is less than 1 g/L, the polymer matrix comprising at least two contiguous zones of distinct rigidities having a rigidity gradient greater than or equal to 0.1 kPa/μm, then b) depositing nano-objects on the surface of the gel, then c) evaporating the solvent from the gel at least until the variation of the rate of evaporation of the solvent from the at least one least rigid zone of the gel is not constant over time, by which the nano-objects migrate towards the at least one most rigid zone of the gel and a gel is obtained for which the surface is at least partially coated with nano-objects, and wherein the density per unit area of nano-objects of the at least one most-rigid zone among the at least two contiguous zones is greater than that of the at least one least-rigid zone among the at least two contiguous zones, the gel that can be obtained and its applications.

9 Claims, 9 Drawing Sheets

(56) References Cited

U.S. PATENT DOCUMENTS

2016/0002368 A1* 1/2016 Gulino ..................... G03F 7/20
                                                                430/269
2016/0325010 A1* 11/2016 Liebler .................. A61L 24/08
2021/0009782 A1* 1/2021 Nicolas .................. C08J 9/365

OTHER PUBLICATIONS

Hong et al, J. Micromechanics and Microengineering, 25, 2015, 045012 (Year: 2015).*
Lee et al, Analytical Chemistry, 75, 2003, 6544-6554 (Year: 2003).*
International Search Report for PCT/EP2019/054859 dated Apr. 25, 2019.
Written Opinion of the International Searching Authority for PCT/EP2019/054859, dated Apr. 25, 2019.
Preliminary Search Report for FR 1851833, dated Nov. 22, 2018.
Tse Jr, et al., "Preparation of Hydrogel Substrates with Tunable Mechanical Properties", Jun. 1, 2010, pp. 10.16.1-10.16.6, Current Protocols in Cell Biology, John Wiley & Sons, Inc, US, vol. 47, No. Suppl. 47, XP002679865.
Zaari N, et al. "Photopol Ymeriza Tion in Microfluidic Gradient Generators: Microscale Control of Substrate Compliance to Manipulate Cell Response", Dec. 1, 2004, pp. 2133-2137, Advanced Materials, Wiley-VCH Germany, DE, vol. 16, No. 23-24.
Kloxin, et al., "In situ elasticity modulation with dynamic substrates to direct cell phenotype", Jan. 1, 2010, pp. 1-8, Biomaterials, Elsevier Science Publishers BV., Barking, GB, vol. 31, No. 1, XP026719454.
Wong, et al., "Directed movement of vascular smooth muscle cells on gradientcompliant hydrogels", Jan. 1, 2003, pp. 1908-1913, Langmuir, American Chemical Society, US, vol. 19, No. 5, XP002513302.
Tsougeni, et al, "Photosensitive Poly(dimethysiloxane) materials for microfluidic applications", Jan. 25, 2007, pp. 1104-1108, Science Direct, Microelectric Engineering, vol. 84, Elsevier B.V.
Hong Vu, "Influence of Pore Size Distribution on Drying Behavior of Porous Media by a Continuous Model", Jul. 16, 1974, pp. 1-172.
Ahmed, "Hydrogel: Preparation, Characterization, and Applications: A Review", Mar. 14, 2013, pp. 105-121, Journal of Advanced Research 2015 (6), Elsevier BV., Cairo University.
Jover, "Variable rigidity surfaces for mechanobiology", ELEN E6945, Device Nanofabrication, Final Paper Assignment 2010.

* cited by examiner

METHOD FOR DEPOSITING NANO-OBJECTS ON THE SURFACE OF A POLYMER GEL COMPRISING ZONES WITH DISTINCT RIGIDITIES

The present invention relates to a method for depositing nano-objects on the surface of a polymeric gel comprising zones of distinct rigidities, this method advantageously making it possible to obtain distinct surface densities in nano-objects, wherein the surface density of nano-objects of the most rigid zones is greater than that of the less rigid zones, the gel likely to be obtained, and its applications.

Application WO 2013/079231 and the articles by Tse et al., Current Protocols in Cell Biology, 47, 2010, 10.16-1-10.6-16, by Zaari et al., Adv. mater. 16, 23-24, 2004, by Kloxin et al. Biomaterials, 31 (1), 2010, 1-8, and by Wong et al., Langmuir, 19 (5), 2003, 1908-1913, describe processes for preparing hydrogels comprising zones of nano-objects with distinct rigidities and whose surface is grafted with proteins and then on which cells are deposited. These processes do not include the water evaporation step of the hydrogels. One of the objectives of these documents is to study the migration, spreading and/or differentiation of cells on the surface of the hydrogel according to the rigidity of its zones. The migrations of cells, which are alive, are induced by the mechanical gradient present on the surface of the hydrogel. In fact, these documents teach that proteins are grafted uniformly on the surface of the hydrogel, and that there is therefore no gradient in surface chemistry.

In many fields, in particular in biology, pharmaceuticals, diagnostics and in the field of sensors, devices comprising a substrate whose surface comprises nano-objects (proteins, nanoparticles, etc.) arranged in a localized manner and therefore having a variable surface density, are sought after. A surface chemistry gradient is thus looked for.

It is relatively easy to locally deposit nano-objects on the surface of a "hard" substrate such as glass or silicon. However, in order to reinforce the bonding forces between the surface and the nano-objects and thus to prolong the life of the device, it is sought to replace the glass or silicon with softer substrates, such as gels based on a polymer matrix, such as hydrogels.

The density of a gel based on a polymer matrix is directly related to its porosity. The more porous a gel, the less rigid it is, and vice versa. In a gel comprising zones of distinct rigidities, the softer zones are the most porous, and the more rigid zones are the least porous.

The literature describes methods for organizing nano-objects on substrates of uniform rigidity/porosity:

- on hydrogel-type substrates: (i) by tamping, (ii) by depositing the molecules through a stencil (iii) by using a microdrop dispenser, or (iv) by activating the surface of the hydrogel by irradiation through a photomask or by a laser.
- on substrates which do not swell in water, such as elastomers, glass, silicon, metals: through self-assembly as a result of the interactions involved during the dewetting of a film of colloidal solution, by evaporation of an emulsion, by evaporation of an organized assembly by a magnetic or optical force, by self-assembly through evaporation in a textured substrate or by tamping.

But these methods may not necessarily be easily transposed to substrates of varying rigidity, or if they are transposable, there is no relationship between the zones on which the nano-objects are deposited and the rigidity of the gel.

The spatial modulation of the chemical affinity of the surface of hydrogels is an issue in the pharmaceutical field, where cell chips are manufactured in order to test the efficacy of drugs on a cell population placed under controlled and reproducible conditions, the most relevant possible with respect to physiological conditions. In addition to the chemistry of the adhesion surface and the geometry imposed on the cells, a key parameter is the rigidity of the substrate, which must approach physiological rigidities (0.1 to 100 kPa). Hydrogels are the only materials covering this range of rigidity. In this context, it is particularly desirable to be able to organize proteins according to chosen patterns on a hydrogel of chosen rigidity.

Techniques for local grafting of proteins by tamping or stencil methods have been described, but they are very limited in that they are not very suitable for grafting onto soft surfaces such as hydrogels. The development of alternative local grafting methods is therefore required.

In the field of diagnostics, biomolecular chips are used to probe the content of biological solutions or serum. Some chips use polymer matrix-based gels or hydrogels as substrate ("Arrayit Microarray hydrogel protein substrates", "Reichert Sensor Chips" for example), because the latter allow a more efficient and robust non-specific adsorption of the molecular probe than a glass surface, especially as the substrate is porous. The molecular probes are deposited using a microdrop dispenser. However, it is very difficult for all the deposits to have identical compositions. Furthermore, as the size of the deposits is micrometric and uniform over the entire chip, the profile of the deposit is circular. This method therefore cannot be used when deposits of varying shapes in geometry or size are desired.

In the field of sensors, the organization of nanoparticles into patterns is a means of performing ultrasensitive detection of analytes by plasmonic detection, of carrying out localized surface chemistry on pre-assembled particles (chemistry of thiols, in particular), or to manufacture local pH or temperature probes when the nanoparticles are deposited on a polymer matrix-based gel such as a hydrogel. The assembly in patterns of nanoparticles is also a means of miniaturizing opto-electronic components such as light generators.

Existing methods for depositing nano-objects on the surface of gels whose surface includes patterns use strategies of directed evaporation of a colloidal solution of nanoparticles to form the desired organizations, such as Langmuir Blodgett, use of a stencil, preliminary organization under an electric or magnetic field, preliminary organization in 3D by the control of physico-chemical interactions. However, the delicate step of directed evaporation is very difficult to implement.

Alternative methods for organizing nano-objects on substrates of varying rigidity/porosity are therefore required.

To this end, according to a first object, the invention relates to a method for depositing nano-objects on the surface of a gel comprising a polymer matrix comprising at least two contiguous zones of distinct rigidities, said method comprising the steps of:
- a) providing a gel comprising a polymer matrix and a solvent within the polymer matrix, the polymer matrix forming a three-dimensional network capable of swelling in the presence of said solvent, where the solubility of the polymer matrix at 1 bar and 25° C. in the solvent, is less than 1 g/L, the polymer matrix comprising at least two contiguous zones of distinct rigidity exhibiting a rigidity gradient greater than or equal to 0.1 kPa/$\mu$m, then b) depositing nano-objects on the surface of the gel, then c) evaporating the solvent from the gel at least until the variation in the rate of evaporation of the solvent from the at least one less rigid zone of the gel is not constant over time, by which the nano-objects migrate towards the at least one more rigid zone of the gel, and a gel is obtained whose surface is at least partially coated with nano-objects, and where the surface density of nano-objects of at least one most rigid zone among the at least two contiguous zones is greater than that of at least one less rigid zone among the at least two contiguous zones.

The method comprises a step a) of providing a gel comprising a polymer matrix and a solvent within the polymer matrix, the polymer matrix forming a three-dimensional network capable of swelling in the presence of said solvent, where the solubility of the polymer matrix at 1 bar and 25° C. in the solvent, is less than 1 g/L.

The gel comprises a polymer matrix and a solvent within the polymer matrix, the polymer matrix forming a three-dimensional network capable of swelling in the presence of said solvent. The polymer matrix is therefore capable of retaining a proportion of solvent within its structure. Generally, the maximum solvent content within the polymer matrix of the gel at 25° C. (calculated as the ratio of the maximum solvent weight to the sum of the maximum solvent weight and the weight of the dry polymer matrix) varies from 20 to 100%, preferably from 38 to 100%. When we continue to add solvent beyond the maximum content, the added solvent is no longer incorporated into the polymer matrix.

The polymer of the polymer matrix of the gel may be homopolymeric (three-dimensional network formed from a homopolymer), copolymeric (three-dimensional network formed from a copolymer), or multipolymeric (three-dimensional network of interpenetrating polymeric gel (IPN)).

Generally, the polymer matrix comprises (or even consists of) a polymer chosen from among:

polyacrylamides;

polyethylene glycols, polypropylene glycols and ethylene glycol or propylene glycol copolymers, optionally comprising patterns resulting from the polymerization of (meth)acrylate compounds;

polysaccharides, optionally comprising repeating units resulting from the polymerization of (meth)acrylate compounds);

(co)polymers resulting from the polymerization of diacrylate and/or (meth)acrylate compounds;

polyvinyl alcohols comprising repeating units resulting from the polymerization of (meth)acrylate compounds;

dextrans comprising repeating units resulting from the polymerization of (meth)acrylate compounds;

polypropylene fumarates and poly (propylene fumarate-co-ethylene glycol);

polysiloxanes, such as poly(dimethylsiloxane) (PDMS); and the combinations of these.

Polymeric matrices based on polyacrylamides, and, in particular, resulting from the polymerization of acrylamide and N,N'-methylenebisacrylamide, are particularly preferred.

The term "(meth)acrylate compounds" means compounds derived from acrylate or methacrylate, for example chosen from among acrylic acid (AA), methacrylic acid (MA), ethylene glycol dimethacrylate (EGDMA), 2-hydroxyethyl methacrylate (HEMA), sulfopropyl acrylate, where the acids may be in the form of a salt, in particular sodium or potassium.

The solvent may be any solvent in which the solubility of the polymer matrix at 1 bar and 25° C. is less than 1 g/L and in which it is capable of swelling.

For example, the solvent may be an aqueous solution or an organic solvent chosen from alcohols, alkanes (pentane, hexane, for example), amines (triethylamine, diisopropylamine, for example), ketones (acetone, for example) and aromatic solvents (toluene, xylene, for example).

In one embodiment, the polymer matrix comprises (or even consists of) polysiloxanes, such as poly(dimethylsiloxane) (PDMS), while the solvent is chosen from among pentane, triethylamine, diisopropylamine or xylene.

The most common solvent is an aqueous solution. The gel is then a hydrogel. Examples of hydrogel are provided in the review by Enas M. Ahmed (Journal of Advanced Research, 2015, 6, 105-121). The polymer matrix then generally comprises (or even consists of) a polymer chosen from among:

polyacrylamides, for example resulting from the polymerization of acrylamide and N, N'-methylenebisacrylamide;

polyethylene glycols, polypropylene glycols and ethylene glycol or propylene glycol copolymers, optionally comprising units resulting from the polymerization of (meth)acrylate compounds;

polysaccharides, optionally comprising repeating units resulting from the polymerization of (meth)acrylate compounds);

(co)polymers resulting from the polymerization of diacrylate and/or (meth)acrylate compounds;

polyvinyl alcohols comprising repeating units resulting from the polymerization of (meth)acrylate compounds;

dextrans comprising repeating units resulting from the polymerization of (meth)acrylate compounds;

polypropylene fumarates and poly(propylene fumarate-co-ethylene glycol fumarate); and the combinations of these.

The solvent may comprise a viscosifying agent, for example glycerol. This agent makes it possible to increase the viscosity of the solvent and therefore to limit its evaporation.

The polymer matrix of the gel used in the process comprises at least two contiguous zones of distinct rigidities exhibiting a rigidity gradient greater than or equal to 0.1 kPa/μm, generally of the order of 1 kPa/μm.

The rigidity of each zone is generally from 100 Pa to 500 kPa, in particular from 0.2 kPa to 100 kPa, preferably from 0.5 kPa to 50 kPa. For example, the more rigid zone(s) has/have a rigidity of 5 kPa to 100 kPa, preferably 5 kPa to 50 kPa and/or the zone(s) the less rigid has/have a rigidity of 0.2 kPa to 10 kPa, preferably 0.5 kPa to 5 kPa.

The local rigidity of each zone of the polymer matrix and the rigidity gradient between two contiguous zones may be determined by atomic force microscopy (AFM), for example by following the protocol described on pages 29 and 30 of application WO 2013/079231. The rigidity gradient is measured on the surface of the zone on which the nano-objects will be deposited during step b).

Generally, the more rigid of the at least two contiguous zones is in the form of a pattern. Between a less rigid pattern and a more rigid zone, there may be levels of increasing rigidity, like "steps of a staircase". Likewise, between a more rigid pattern and a less rigid zone, there may be steps of decreasing rigidity. The boundary between the less rigid and more rigid regions is usually a line or a circle. Advantageously, the geometry of the pattern(s) is specific (square, circular, triangular, hexagonal, etc.). Its size may range from a few hundred nanometers to several centimeters, typically from 10 μm to 10 mm.

The surface of the gel may include alternating rigid patterns and soft patterns. Alternatively, the surface of the gel may comprise several rigid patterns located in a soft continuous matrix.

Hydrogels of which the polymer matrix comprising at least two contiguous zones of distinct rigidities exhibiting a rigidity gradient greater than or equal to 0.1 kPa/μm may, for example, be prepared by photopolymerization by following the process described in application WO 2013/079231.

Polysiloxanes comprising zones of distinct rigidities are also known from Roger Piqueras Jover ("Variable rigidity surfaces for mechanobiology") (polymerization by chemical means using electronic lithography to increase the number of bonds formed), or from K. Tsougeni, A. Tserepi and E. Gogolides (Microelectronic Engineering 84 (5-8), 1104-1108 (2007)) (photosensitive deep UV polymerized PDMS).

The method comprises a step b) of depositing nano-objects on the surface of the gel. The nano-objects are preferably chosen from among:

proteins, peptides and their mixtures, polysaccharides, and nanoparticles, in particular metal, semiconductor or polymer nanoparticles.

Nano-objects may be bacteria.

Nano-objects are generally not cells. In one embodiment, the nano-objects are not living organisms.

The metal, in particular, may be chosen from among alkali metals, alkaline earth metals, lanthanides, actinides, transition metals and so-called "poor" metals, but is preferably chosen from gold, silver and indium.

The semiconductor may be, for example cadmium telluride (CdTe).

The polymer nanoparticles may, for example, be made of polystyrene or of latex.

Proteins, peptides, polysaccharides and mixtures of these are the preferred nano-objects, in particular proteins and/or peptides inducing cell adhesion via integrins, such a protein possibly being fibronectin, collagen, laminin or peptides of the RGD type.

The prefix "nano" means that the average diameter of the nano-object lies between 1 and 1000 nm, in particular from 2 to 500 nm, for example from 2 to 250 nm. Gold nanoparticles typically have average diameters of 5 to 400 nm. Nanoparticles of silver or indium typically have average diameters of 2 to 10 nm.

The average diameter of the nano-object is therefore greater than the average diameter of the pores present on the surface of the gel (of the order of 1 angstrom), which allows the nano-objects to remain on the surface of the gel and not to sink into the polymer matrix, or only slightly.

The average pore diameter of the gel may be measured by neutron scattering or small angle X-rays.

The average diameter of proteins, peptides or polysaccharides is typically measured by gel electrophoresis. The average diameter of the nanoparticles is typically measured by Transmission Electron Microscopy (TEM) or Scanning Electron Microscope (SEM).

Generally, during step b), the nano-objects are deposited in the form of a mixture comprising the nano-objects and a solvent. The solvent for this mixture may be the same or different from the solvent for the gel. Preferably, the solvent of the mixture is soluble in the solvent of the gel (soluble under the conditions of step b)). Preferably, the solvent of the mixture is identical to the solvent of the gel.

The mixture may be colloidal (the nano-objects being in suspension).

The method may comprise, between steps b) and c), a step b1) consisting in leaving the nano-objects in contact on the surface of the gel, generally for a period of 1 min to 24 hours, in particular 1 min to 12 hours, by example 5 min to 1 hour. When the nano-objects are proteins, this step corresponds to an incubation. Generally, whatever the duration of this contacting, there is a difference in surface density of nano-objects between the rigid and soft zones on the gel obtained at the end of the process. A longer duration may make it possible to deposit more nano-objects on the surface (more nano-objects simultaneously on the rigid and soft zones, but the difference in surface density in nano-objects between the rigid and soft zones exists regardless of this duration).

The method may also comprise, between steps b) and c), (and after the optional step b1) if it is present), a step b2) consisting in removing part of the nano-objects from the surface of the gel. Generally, the nano-objects are deposited in the form of a mixture comprising the nano-objects and a solvent, wherein step b2) may be carried out by aspirating the supernatant solution above the surface of the gel, for example with a pipette.

The method comprises a step c) of evaporating the solvent from the gel at least until the variation in the rate of evaporation of the solvent from the at least one less rigid zone of the gel is not constant over time. This step leads to the migration of the nano-objects towards the at least one most rigid zone of the gel, and therefore to the obtaining of a gel whose surface density of nano-objects of at least one of the most rigid zones among the at least two contiguous zones, is greater than that of at least one less rigid zone among the at least two contiguous zones.

Figure 2:
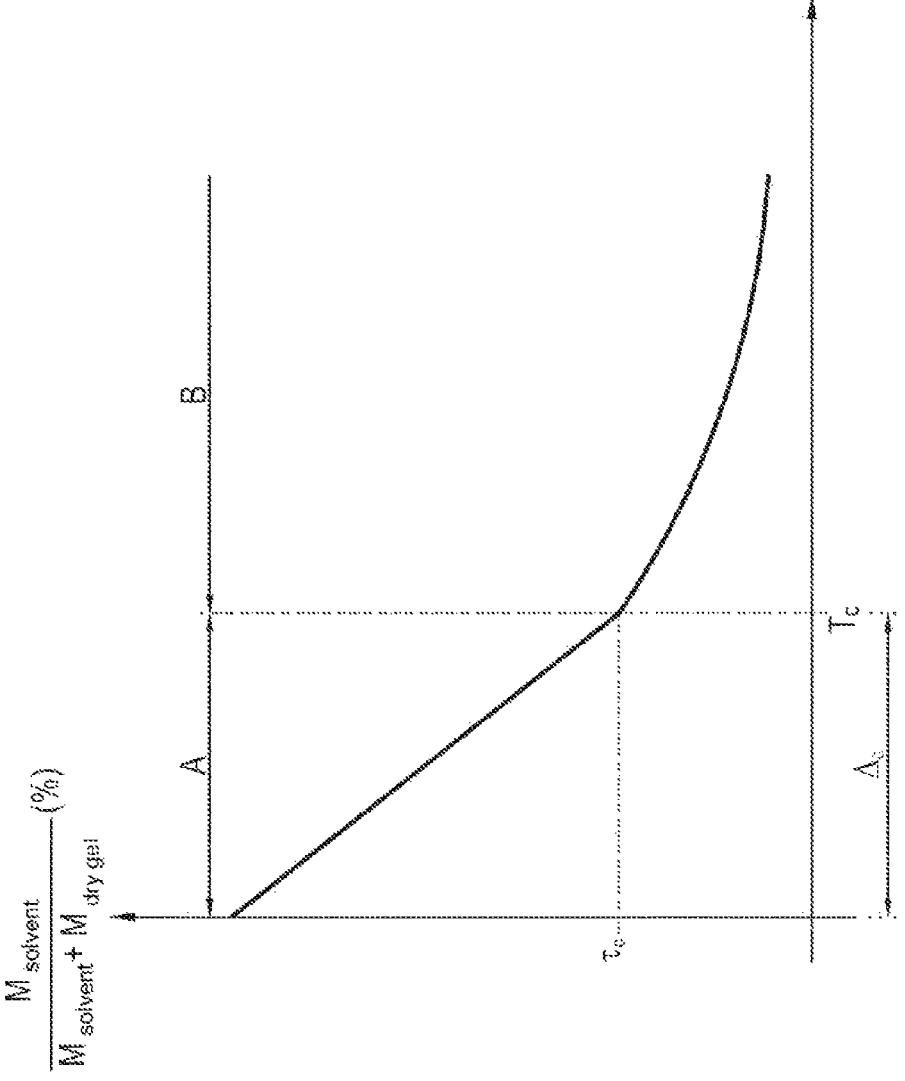

Evaporation of the solvent from a gel of uniform density involves two regimes which are illustrated in FIGS. 1 and 2.

During the first evaporation period ("A" in FIGS. 1 and 2), solvent is continuously removed from the gel surface by capillary forces and the solvent content decreases at a constant rate, which is explained by the fact that the gel surface is sufficiently wetted by the solvent to behave like the surface of a liquid. Its evaporation rate is equal to that of a liquid surface, which depends only on the gas used for drying and the transfer coefficient of the boundary layer of the gel surface.

When evaporation is continued, the evaporation rate reaches a critical evaporation rate at a critical evaporation time $T_c$ which marks the transition between the first and second periods of evaporation.

During the second period of evaporation ("B" in FIGS. 1 and 2), the diffusion forces become predominant over the capillary forces and the removal of the solvent from the gel is mainly controlled by the diffusion of the solvent into the pores of the gel towards its surface. The solvent evaporation rate is not constant over time. It decreases until an equilibrium evaporation rate is reached beyond which the gel can no longer be dried.

The critical evaporation time $T_c$ is the minimum time as of which the rate of evaporation of the solvent is not constant over time when the solvent from the gel is evaporated.

The critical evaporation time $T_c$ is a characteristic of each gel.

It depends on the nature of the solvent and its possible additives (when the solvent is an aqueous solution, $T_c$ depends on the salinity, on the pH, on the ionic strength of this solution). For example, the critical evaporation time $T_c$ of a gel whose solvent comprises a viscosifying agent is greater than that of a gel comprising the same polymer matrix and the same solvent, but free of a viscosifying agent. The addition of a viscosifying agent to the solvent therefore makes it possible to increase the critical evaporation time $T_c$ and the duration of the first evaporation period.

When the solvent is an aqueous solution (the gel then being a hydrogel), the evaporation of the solvent is dehydration. The critical evaporation time $T_c$ is then the critical dehydration time $T_c$, which corresponds to the minimum time from which the rate of dehydration of the at least one less rigid zone of the hydrogel is not constant over time when the hydrogel is dehydrated.

The critical evaporation time $T_c$ also depends on the polymer matrix, namely on the nature of the polymer, but also on its porosity and therefore on its rigidity. The critical evaporation time $T_c$ is therefore not identical between the most rigid and least rigid zones of the gel. In step c), the evaporation is continued at least until the variation in the rate of evaporation of the solvent from the at least one less rigid zone of the gel is not constant over time. It is therefore the variation in the rate of evaporation of the solvent from the at least one least rigid zone of the gel that is to be considered. In addition, the "at least until the variation in the rate of evaporation of the solvent is not constant over time" means that the evaporation of the solvent from the at least one less rigid zone of the gel is continued at least until the critical evaporation time $T_c$, so that the evaporation rate of this at least one least rigid zone is in the second evaporation period. Referring to FIGS. 1 and 2, during step c), the evaporation of the at least one least rigid zone of the gel is continued at least until $T_c$, or beyond, in the second evaporation period "B". Also, step c) generally amounts to evaporating the solvent from the gel for a time greater than the critical evaporation time $\Delta c$, where the critical time $\Delta c$ is the time between the start of evaporation and the critical evaporation time $T_c$ of the at least one least rigid zone of the gel.

To determine whether the variation over time in the rate of evaporation of the solvent from the at least one least rigid zone of the gel is constant over time or not, it suffices to:
   i. prepare a gel:
   of which the polymer of the polymer matrix is identical in nature to that of the polymer matrix of the gel used in the process according to the invention,
   the solvent of which is identical to the solvent of the gel used in the process according to the invention (including the possible presence of additives such as a viscosifying agent), and
   the density of which is equal to that of the at least one least rigid zone of the gel used in the process according to the invention.

The gel thus prepared therefore has a uniform density, unlike the gel used in the process according to the invention. The critical evaporation time $T_c$ of the prepared gel is therefore identical in all zones of the gel.
   ii. then evaporate the solvent from the prepared gel, this evaporation being carried out under the same conditions as those in step c), and by measuring either the solvent content or the rate of evaporation of the solvent over time, and plot:
   the curve of the average evaporation rate as a function of time and determine the time as of which the evaporation rate is not constant (FIG. 1), or
   the curve of the solvent content as a function of time and determine the time from which the derivative of the solvent content is not constant (FIG. 1), or FIG. 1.3 p. 11 of the thesis of Thai Hong Vu defended in 2006

"Influence of Pore Size Distribution on Drying Behavior of Porous Media by a Continuous Model", Fakultät für Verfahrens- und Systemtechnik der Otto-von-Guericke-Universität Magdeburg, Germany).

These curves therefore make it possible to determine the critical evaporation time $T_c$ as of which the second evaporation period begins for the at least one least rigid zone of the gel used in the process according to the invention, and therefore to determine from when, under the evaporation conditions of step c), the variation in the rate of evaporation of the solvent from the at least one least rigid zone of the gel is not constant over time.

The method according to the invention, and the determination of "at least until the variation in the rate of evaporation of the solvent from the at least one least rigid zone of the gel is not constant over time", do not require that the evaporation conditions (nature of the gas, gas flow rate, pressure, and/or temperature of the gas) are constant during step c). It suffices only that the evaporation of step ii) used to determine "at least until the variation in the rate of evaporation of the solvent from the at least one least rigid zone of the gel is not constant over time" is carried out under the same conditions as those of step c).

By "evaporation carried out under the same conditions as those of step c)" is meant that the surface zone of the gel used in step ii) is identical to ±10% of that of the surface of the gel implemented in step c), the thickness of the gel used in step ii) is identical to ±10% of that of the gel used in the process according to the invention, and that, at all times "t" of the evaporation of step ii):
   the gas used to evaporate is identical to that used in step c) and/or the pressure is ±10% identical to that of step c) (if the evaporation of step c) is carried out under vacuum, the vacuum is identical to ±10% for the evaporation of ii)),
   the speed of the gas brought into contact with the prepared gel is identical to ±10% of the gas flow rate at time tin step c), and
   the temperature of the gas used to evaporate is identical to ±2° C. of the temperature of the gas used to evaporate at time tin step c).
   Usually, during step c):
   evaporation is carried out by bringing the gel into contact with a gas which is air or an inert gas (such as nitrogen or argon), preferably air, and/or
   the pressure is 0.1 to 1 bar, preferably 1 bar, and/or
   the temperature of the gas brought into contact with the gel is 4 to 90° C., in particular 10 to 70° C., preferably 15 to 35° C., in particular at room temperature (20° C.), and/or
   the speed of the gas flow brought into contact is between 0 and 4 m/s, in particular from 0 to 1 m/s, preferably of the order of 0.45 m/s (for example, when the gel is placed under a laminar flow hood), these conditions being independently constant over time or variable over time during step c).
   Preferably, at least until the critical evaporation time $T_c$ of the at least one least rigid zone of the gel, or even during the duration of step c), the evaporation conditions are constant over time, i.e.:
   when evaporation is carried out by bringing the gel into contact with a gas:
   the nature of the gas remains the same over time,
   the gas flow rate is constant at ±10%, and
   the gas temperature is constant at ±2° C., and
   the (de)pressurization is constant at ±10% over time (where (de) pressurionization means pressurization (P≥1 bar)) or depressionization (P<1 bar), for evaporation under vacuum for example).

Generally, at the start of step c) (when the evaporation has started), the gel has a solvent content $t_a$ greater than the solvent content $t_c$ of the gel at the critical evaporation time $T_c$ of the at least one zone least rigid of the gel. The solvent content is thus such that, at the start of step c), the variation in the rate of evaporation of the solvent from the at least one least rigid zone of the gel is constant over time. At the beginning of step c), the evaporation of the at least one least rigid zone of the gel is in the first evaporation period defined above. In practice, this condition is almost always true when the nano-objects are deposited as a mixture comprising the nano-objects and a solvent.

The invention is based on the discovery that controlling the rate of evaporation of the solvent when the nano-objects are attached to the surface of the gel having a rigidity (or porosity) gradient makes it possible to control the distribution of the nano-objects and therefore their surface density. More precisely:

If the evaporation of the solvent from the gel is stopped while the variation in the evaporation rate of the solvent from the at least one least rigid zone of the gel is constant over time, the distribution of the nano-objects is homogeneous at the surface of the gel, If the evaporation of the solvent from the gel is carried out at least until the variation in the rate of evaporation of the solvent from the at least one least rigid zone of the gel is not constant over time, the nano-objects are selectively attracted to the more rigid regions, i.e. regions of lower porosity.

The final distribution of the nano-objects is thus controlled by the rate of evaporation of the gel when the nano-objects are attached.

Without wishing to be bound by a particular theory, the inventors suppose that the control of the surface density would be explained by the following. By its structure, the gel used in the process is a porous material, the swelling rate of which varies with the solvent content. Depending on the solvent content, a gel brought into contact with nano-objects absorbs the solvent to reach its swelling equilibrium. In doing so, it concentrates the nano-objects contained in the solvent on its surface. For example, in the case of a hydrogel based on polyacrylamide, the water and protein diffusion coefficients are respectively of the order of $10^{-10}$ and $10^{-12}$ $m^2$/s. Proteins thus penetrate at least 10 times slower than water in a polyacrylamide hydrogel. The swelling of the hydrogel in the presence of a solution of nano-objects will therefore result in the concentration of the nano-objects on its surface. At this stage, the distribution of nano-objects is linked to the convective forces associated with the pumping of regions of different porosities of the hydrogel, to the weight of the nano-objects, to the forces interacting with the surface and to the entropic forces which tend to standardize the distribution of the nano-objects. In the case of a gel comprising at least two contiguous zones of distinct rigidities, the critical evaporation time $T_c$ varies spatially, with the porosity/the rigidity: the solvent of the most rigid regions, the pores of which are of smaller size, evaporates more slowly. Consequently, by a dewetting phenomenon, the nano-objects located in the softer regions, where the pores are of larger size, are carried away through the surface tension forces towards the regions still solvated. Thus, when the solvent of a gel comprising at least two contiguous zones of distinct rigidities is evaporated beyond the critical evaporation time $T_c$ from its most porous/least rigid regions, the nano-objects distributed on its surface are displaced towards the less porous/more rigid regions. It is this phenomenon that the present invention uses to concentrate the nano-objects in the most rigid regions on the surface of gels comprising at least two contiguous zones of distinct rigidities.

The effect of concentration of nano-objects on the most rigid/less porous regions is all the more marked as the rigidity/porosity gradient is strong. Furthermore, rigidity gradients of less than 0.1 kPa/μm between the contiguous zones lead to gels in which the difference in surface density of nano-objects is too low for most applications. This is why the process uses gels with a higher rigidity gradient.

The process therefore relies on moving the nano-objects to the less porous/more rigid regions during evaporation. In order to avoid hindering this movement, it is preferable that there is no adhesive interaction between the surface of the gel and the nano-objects, in particular that the nano-objects and the polymer matrix of the gel are not linked by covalent binding, and/or by a adhesive bond, which may be effected by an appropriate choice of the polymer and of the nano-objects (and, in particular, of the possible functions which they carry) so that such bonds do not exist. The presence of adhesive bonds may be characterized by AFM and measurement of the force profile. The surface tension force is generally greater than the adhesion force as measured by AFM. The surface tension force requires knowledge of the ratio of surface tensions present in Young Dupré's law, this ratio being able to be measured, for example, by a contact angle at equilibrium experiment (without gas flow, in particular of air). Measuring the contact angle then makes it possible to measure the surface tension force.

There was a technical prejudice to be overcome in order to achieve the process according to the invention. In fact, those skilled in the art avoid evaporating the solvent from the gel, because they expect degradation, in particular by cracking/fracturing. Additional technical prejudices existed when the nano-objects are proteins. This is because those skilled in the art generally avoid evaporating the solvent from the gel, as they expect degradation of the proteins if they run dry. This is because most protein suppliers recommend avoidance of drying a protein that has been dissolved in order to avoid denaturing it. However, surprisingly, such denaturation is generally not observed in the process according to the invention.

During step c), at the start of evaporation, the content of inorganic salts in the solvent of the gel is preferably less than 6 g/L, in particular less than 5 g/L, typically less than 4 g/L, for example less than 3 g/L, preferably less than 2 g/L, a content of less than 1.5 g/L, or even less than 1.0 g/L, or even less than 0.5 g/L being particularly preferred. Preferably, during step c), the solvent is free from inorganic salts.

Chloride salts (NaCl, KCl, $CaCl_2$) and/or $MgCl_2$), phosphate salts ($Na_2HPO_4$ and/or $K_2HPO_4$), carbonate salts ($NaHCO_3$) are examples of inorganic salts. These are conventionally used in physiological aqueous and/or buffer solutions used as a solvent in hydrogels and for proteins.

Generally, the user knows the mineral salt content at the start of evaporation, because the mineral salt content in the gel supplied in step a) and the content of mineral salts possibly added during step b) is known, (these mineral salts may, in particular, come from the solvent of the mixture comprising the nano-objects and a solvent deposited during step b)). If the mineral salt content is unknown, it may be determined by ion chromatography.

Degradation by cracking/fracturing of the gel during evaporation is generally not observed when the mineral salt content is as mentioned above. Without wishing to be bound by a particular theory, the inventors note that the mineral salts, present at higher contents, crystallize during the evaporation of the solvent, which leads to cracking of the gel, in particular during its re-swelling with a view to its use in solvated form, and in general, leads to the presence of numerous deposits and immovable crystals on the surface. Preferably, during step c), the solvent is free from a compound capable of crystallizing under the conditions of step c).

In addition, those skilled in the art are accustomed to using proteins in physiological media, which are aqueous solutions, generally buffered, and whose mineral salt content exceeds that mentioned above. Using a solvent with a salt content as defined above is very unusual for those skilled in the art.

The method may comprise, before step a), the steps consisting of:

a0) providing a gel having an initial solvent content $t_i$ greater than the solvent content $t_a$, then a0') evaporating the solvent from the gel to the initial solvent content $t_a$, wherein a gel as defined in step a) is obtained.

The evaporation of step a0') is therefore carried out before the deposition of the nano-objects. This prior evaporation makes it possible to reduce the thickness of the solvent layer on the surface of the gel and thus to promote the migration by convection of the nano-objects towards the surface of the gel during step b) which follows.

When the nano-objects are proteins and/or peptides and/or polysaccharides, the process may comprise, after step c), a step d) of covalent grafting of proteins and/or peptides and/or polysaccharides on the gel, which makes it possible to immobilize them definitively and prevents the peptides and/or proteins and/or polysaccharides from moving again on the surface of the gel, during rinsing of the gel, for example. The proteins and/or peptides and/or polysaccharides deposited during step b) may have been modified beforehand so that they carry a function capable of reacting with the polymer matrix of the gel.

The method may comprise, after step c), or step d) if it is present, a step e) of rinsing with a solvent. This solvent may be the same or different from the gel solvent. The rinsing step may be repeated.

The method may comprise, after step c), or, if they are present, after step d) or e), a step f) of recovering the gel, the surface density of which in nano-objects of at least one most rigid zone among the at least two contiguous zones, is greater than that of at least one least rigid zone among the at least two contiguous zones. The method for measuring the surface density in nano-objects varies according to the nature of the nano-objects. For example, when the nano-objects are proteins, it is possible to use a primary antibody capable of recognizing said protein, then a secondary antibody capable of recognizing said primary antibody, this secondary antibody being bound to a fluorophore, then analyzing the surface density by confocal microscopy fluorescence. When the nano-objects are nanoparticles, the surface density may be analyzed by scanning electron microscopy.

The method according to the invention is easy to implement. It does not require complex equipment. It does not require directed evaporation such as Langmuir Blodgett.

It may be implemented with patterns for rigid and/or soft zones of any size and shape. The geometry of the patterns is specific, unlike the deposits obtained with a microdrop dispenser.

The method according to the invention makes it possible to concentrate the nano-objects on the more rigid zone(s), which would be very difficult to obtain using the techniques of tamping, stenciling, microdrop dispensing, or laser which would require an alignment step between the texture in rigidity and the modulation of the surface chemistry, a technologically demanding step: it would consist in alignment with a resolution of the order of a micron of the reliefs respectively of tamping, stenciling, positioning of the nozzle of the microdrop dispenser or the laser beam taking into account the rigidity patterns already present in the gel, which is technologically achievable but difficult and time consuming.

The method according to the invention makes it possible to maintain the integrity of the gel, including its least rigid zones. On the contrary, the tamping and stencil technologies are unsuitable for rigidities of the order of kPa because they physically degrade the surface. As for surface activation methods through a photomask, the UV used to activate the surface modifies the rigidity/porosity of the hydrogel itself textured by photopolymerization. In fact, the surface activation process required to graft the molecules prohibits the rinsing of the hydrogel necessary to remove its photoinitiator, and therefore stabilize its mechanical properties. Finally, the topographic texturing of the hydrogel to trap nano-objects has, to the knowledge of the inventors, never been carried out while preserving both the desired topography and the local porosity/rigidity, either because of the swelling of the hydrogels (the holes fill up because the walls are deformed), or because the process of creating the topography is done by laser and locally hardens the hydrogel through thermal deterioration (surface crust).

The method according to the invention is inexpensive. The organization of nano-objects by porosity gradient is a low cost technology compared to the purchase of a microdrop dispenser.

According to a second object, the invention relates to the gel capable of being obtained by the process defined above, said gel comprising a polymer matrix comprising at least two contiguous zones of distinct rigidities, the surface of the gel being at least partially coated with nano-objects, wherein the surface density of nano-objects of at least one most rigid zone among the at least two contiguous zones is greater than that of at least one least rigid zone among the at least two contiguous zones.

The nano-object concentration gradient between the at least one more rigid zone and the at least one least rigid contiguous zone may be quantified by Fourier transform of the intensity profile. The pattern of the at least one more rigid zone being generally periodic, as the surface density of nano-objects is not homogeneous, a peak linked to the repetition of the pattern emerges from the measurement noise. When the pattern is not periodic, the intensity histogram makes it possible to determine the difference in surface distribution in nano-objects between the most rigid zone and the least rigid zone: if the surface distribution in nano-objects is uniform, the histogram must be Gaussian. If it is heterogeneous, we will have two Gaussians. In this case, the criterion to determine that it is heterogeneous is the Shannon criterion: the two peaks must be separated by more than the sum of the ½ widths of each Gaussian.

This gel has very variable applications depending on the nature of the nano-objects deposited on the surface. According to a third object, the invention relates to the use of this gel as a photonic sensor (typically when the nano-objects are semiconductors) or physicochemical, for example as a pH sensor (typically when the nano-objects are gold particles)

or temperature (typically when the nano-objects are CdTe particles), as a sensor for analyte detection, as a protein or peptide chip (typically when the nano-objects are proteins and/or peptides), as cell chips or as a biomolecule capture chip.

The invention also relates to:

a cell positioning method for screening active pharmaceutical ingredients comprising bringing pharmaceutical active ingredients into contact with the gel according to the invention in which the nano-objects are peptides or proteins, a method for capturing biomolecules comprising contacting a medium comprising biomolecules to be captured with the gel according to the invention in which the nano-objects are peptides or proteins, an analysis method comprising bringing a medium comprising an analyte to be detected into contact with the gel according to the invention.

The figures and examples below illustrate the invention.

FIG. 1: Schematic curve of the mass loss per unit zone per unit time (dM/dt/S) in kg/s/m$^2$ of a gel of uniform density as a function of time in minutes.

FIG. 2: Schematic curve of the solvent content (Msolvent/(Msolvent+M dry gel)) (%) of a gel of uniform density as a function of time in minutes.

Figure 3:
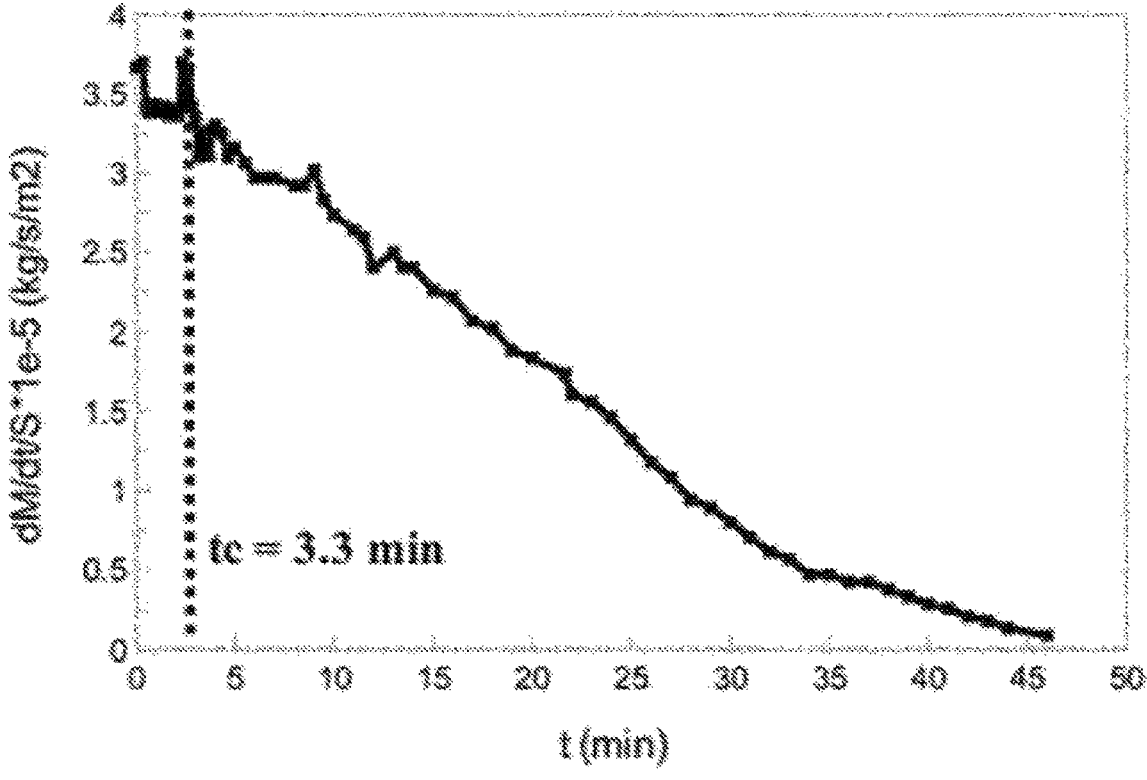

FIG. 3: Curve of mass loss per unit zone per unit time (dM/dt/S) in kg/s/m$^2$ of a gel of uniform density of 3.3 kPa as a function of time in minutes.

Figure 4:
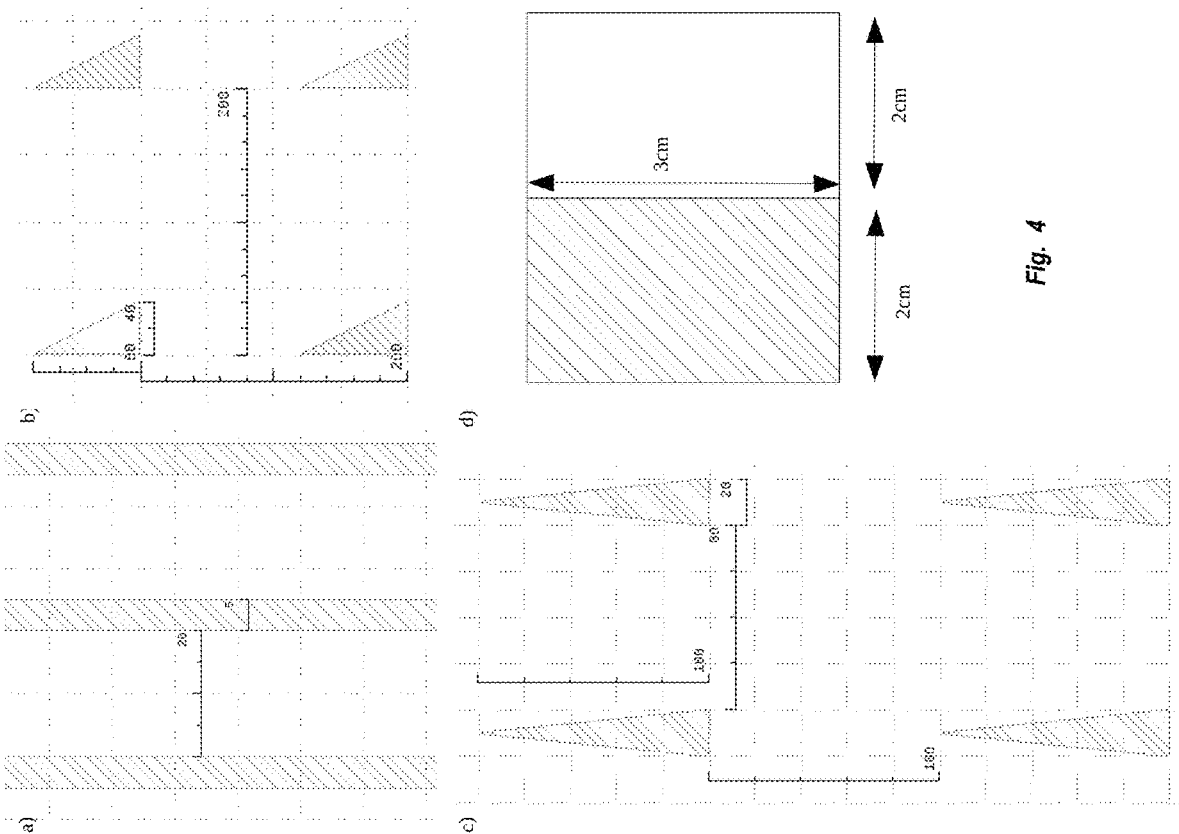

FIG. 4: Patterns and rigidity profiles used to prepare the hydrogels comprising two contiguous zones of distinct rigidities used in the examples.

Figure 5:
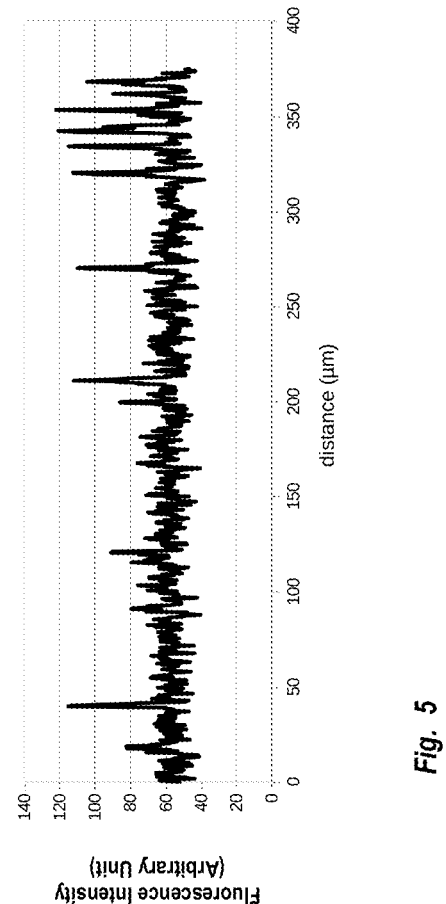

FIG. 5: Fluorescence intensity (arbitrary unit) as a function of the distance ($\mu$m) of the gel obtained by the method of Comparative Example 1.

Figure 6:
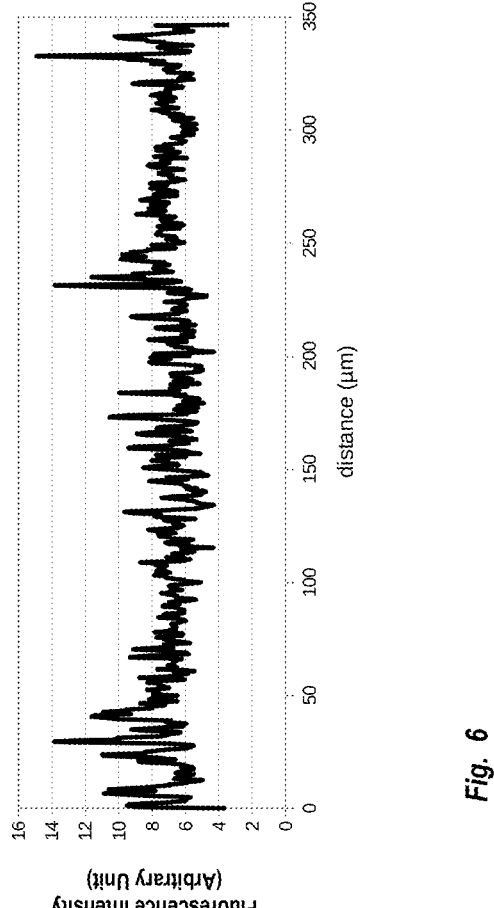

FIG. 6: Fluorescence intensity (arbitrary unit) as a function of the distance ($\mu$m) of the gel obtained by the method of Comparative Example 2.

Figure 7:
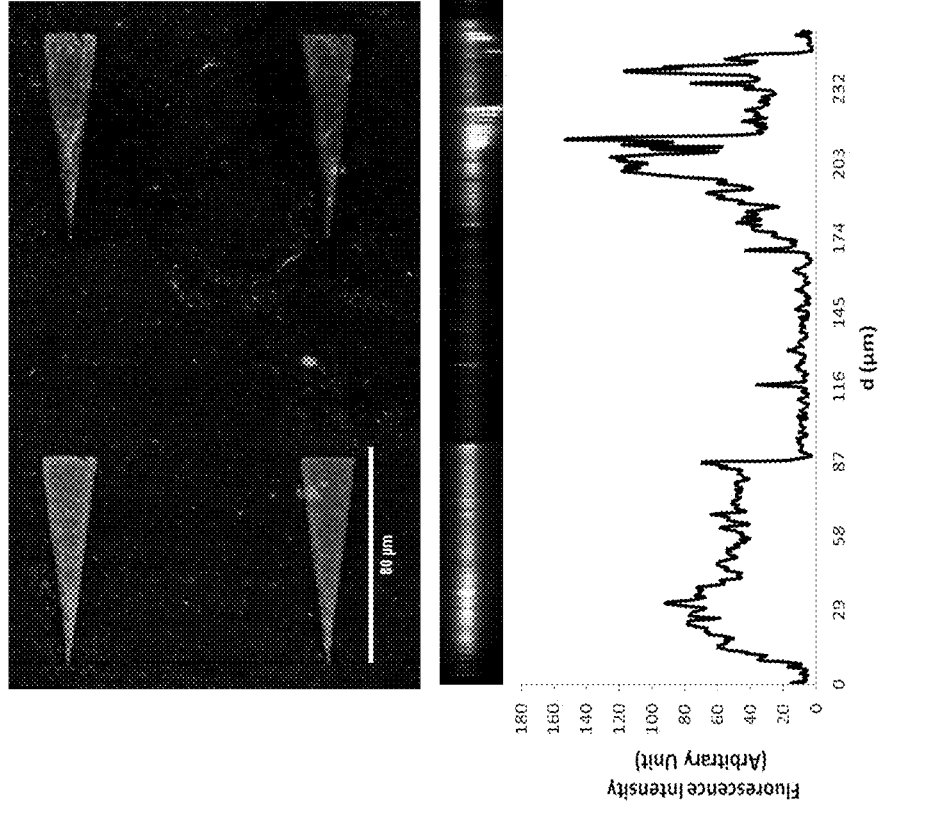

FIG. 7: A) Immunofluorescence image taken by confocal microscopy of fibronectin fixed on a polyacrylamide hydrogel exhibiting an alternation of hard triangular patterns (10 kPa) of 20×100 $\mu$m spaced 100 $\mu$m in a softer matrix (3 kPa) of the gel obtained by the method of Example 3. The variations in fluorescence intensity in the thickness of the hydrogel are visualized along the white dotted line and plotted on the underlying panel.

B) Fluorescence intensity (arbitrary unit) as a function of the distance ($\mu$m) from the gel obtained by the method of Example 3.

Figure 8:
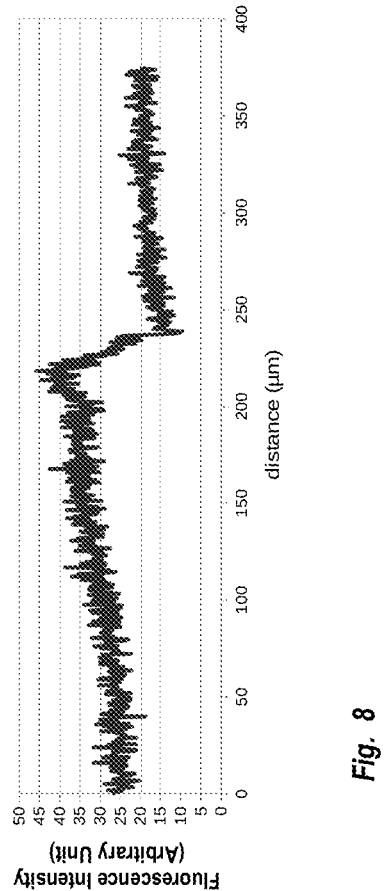

FIG. 8: Fluorescence intensity (arbitrary unit) as a function of the distance ($\mu$m) of the gel obtained by the method of Example 4.

Figure 9:
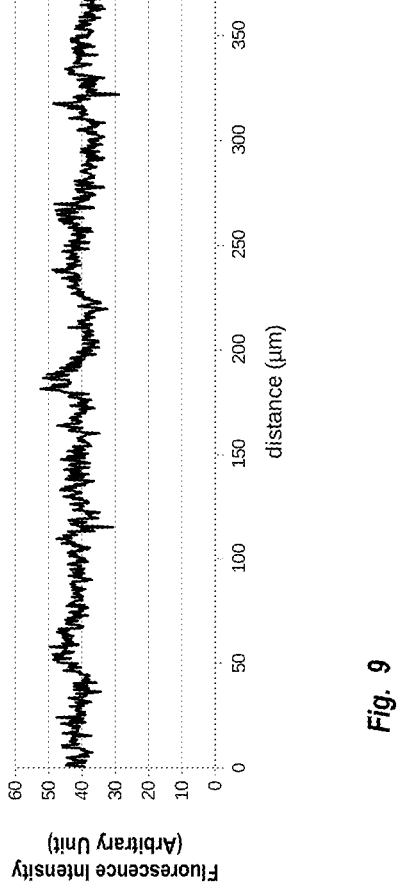

FIG. 9: Fluorescence intensity (arbitrary unit) as a function of the distance ($\mu$m) of the gel obtained by the method of Comparative Example 6.

EXAMPLES

The examples were carried out with polyacrylamide hydrogels. The gels used in the examples below have two contiguous zones of distinct rigidity. For each, the critical dehydration time $T_c$ of the least rigid zone is a few minutes and may be determined as follows.

Determination of critical evaporation time $T_c$ of gels of uniform densities.

Gels were prepared from the following compositions:

Composition:

10% acrylamide (250 $\mu$l of initially 40% solution)

0.5% N,N'-methylenebisacrylamide (250 $\mu$l of initially 2% solution)

0.2% Irgacure 819 w/v (Ciba, photoinitiator)

1% propylamine (initiator)

deionized water (490 $\mu$l).

Irgacure 819 is weighed in a UV-opaque bottle. We add propylamine. The whole is heated at 50° C. for 2 minutes. After heating, a homogeneous, transparent solution is obtained. Water, acrylamide, and bis acrylamide are added quickly. The whole is homogenized gently with a pipette, to limit the incorporation of oxygen.

Gels with a density of 3.3, 11.8 or 24.7 kPa were thus prepared.

Evaporation was carried out at 21° C., without gas flow (evaporation in air, in the cage of a caged precision balance (Denver Summit 110 G/0.1 MG) which allowed continuous measurement.

In the three cases, we plotted the curve of the average evaporation rate as a function of time for a surface of 7 cm$^2$ and an inflated thickness of the order of 50 $\mu$m (FIG. 3 for the gel with a rigidity of 3.3 kPa), which made it possible to determine the critical evaporation times $T_c$ provided in Table 1. In this case, it is a question of critical rate of dehydration because the gels are hydrogels.

TABLE 1

| Critical dehydration time $T_c$ of acrylamide hydrogels of uniform densities | |
| --- | --- |
| density Y(kPa) | $T_c$ (min) |
| 3.3 | 3.3 ± 0.3 |
| 11.8 | 6.5 ± 0.3 |
| 24.7 | 8.1 ± 0.2 |

The nano-objects used in the examples below are:

either gold nanoparticles, 10 nm in diameter. The nanoparticles are simply adsorbed on the surface of the gel, without subsequent covalent grafting.

or fibronectin, coupled to a hetero-bifunctional crosslinking agent responsible for ensuring covalent grafting between the protein and the gel by linking the primary amine functions of and the amide functions of the gel.

Comparative Example 1: Method in which the proteins are deposited on a dry gel ($t_a < t_c$) and method without a dehydration step after the protein has been deposited: obtaining a uniform distribution of proteins.

A porosity-modulated polyacrylamide hydrogel covalently fixed to a glass slide was prepared by gray-level photolithography according to the process described in application WO 2013/079231 and detailed below.

The pattern represented in FIG. 4 by the reference "a" was used. The polyacrylamide hydrogel exhibited alternating hard bands (8.5 kPa) 5 $\mu$m wide and softer bands (3.5 kPa) 20 $\mu$m wide.

a) Preparation of Basal Glass Slides

The basal glass slide, with a diameter of 30 mm, is cleaned in a solution of 0.1 mol/L of sodium hydroxide for 10 min. It is then rinsed intensively with water, then with ethanol, and dried in air. 500 $\mu$l of a silane solution comprising 56 $\mu$l of Bind-Silane (GE Healthcare), 484 $\mu$l of 10% acetic acid, and 14.46 mL of ultra pure ethanol are deposited on the slide and rubbed with a knitted cloth of polyester until all traces of solution disappear. A glass slide is thus obtained having aldehyde functions at its surface, which allows covalent grafting of the polyacrylamide gel.

b) Preparation of the Gray Level Mask

The grayscale mask is the master copy of the rigidity profile that will be transferred to the hydrogel. Here is transferred the pattern shown in FIG. 4 by the reference "a".

An optical microscopy slide (26 mm×76 mm) is washed in a solution of hydrogen peroxide/concentrated sulfuric acid in proportions 1:2, for 10 minutes. On this slide, 1 nm of titanium then 9 nm of chromium are deposited using a Plassys type electron gun evaporator. A resin of the AZ1512HS type (available from Clariant) diluted to 50% in its AZ-EBR solvent (which is a propylene glycolmonomethyl ether acetate solvent) is deposited on the slide on the chrome side using a spinner at a rate of 3000 rpm for 30 seconds, wherein a resin thickness of 600 nm is obtained. It is illuminated through a Sodalime mask presenting the desired patterns. After development, the slide is placed in a DPS type etching reactor, and etched for 30 seconds using a chlorine treatment ($\frac{2}{3}$ Cl$_2$:$\frac{1}{3}$ O$_2$) Under a Pressure Between 1.33 and 3.33 Pa (10 and 25 mTorr). The resin is removed by an O2 plasma for 30 seconds in the DPS reactor. The slide is then made hydrophobic by an Optool treatment (Daikin DSX): immersion for 1 minute in Optool diluted to 1/1000 in perfluorohexane. The slide is then left for 1 hour in water vapor at 80° C. Finally, it is immersed with slow stirring for 10 minutes in perfluorohexane.

c) Preparation of the Hydrogel

Composition:

10% acrylamide (250 µl of initially 40% solution)

0.5% N,N'-methylenebisacrylamide (250 µl of initially 2% solution)

0.2% Irgacure 819 w/v (Ciba, photoinitiator)

1% propylamine (initiator)

deionized water (490 µl).

Irgacure 819 is weighed in a UV-opaque bottle. We add propylamine. The whole is heated at 50° C. for 2 minutes. After heating, a homogeneous, transparent solution is obtained. Water, acrylamide, and bis acrylamide are added quickly. The whole is homogenized gently with a pipette, to limit the incorporation of oxygen. 30 µL are deposited on the 30 mm glass slide pretreated according to the above protocol. The slide is placed on a sample holder having spacers which maintain a spacing of 40 µm between the slide and the chrome mask, deposited on the spacers. The assembly (mask, solution, slide) is illuminated using an Eleco UVP281 fiber lamp (2 W/cm$^2$) for 16 s. This assembly is then immersed in water to detach the mask from the hydrogel using forceps.

The hydrogel is rinsed 3 times with deionized water and stored in deionized water.

d) Characterization of the Rigidity of the Hydrogel

The relative variation in porosity of the different regions of the hydrogel is estimated by measuring the local rigidity of the hydrogel. The local rigidity of the gel is measured using an AFM in aqueous medium (JPK brand). The resistance of the gel to penetration of the point is recorded. A 34 µm×20 µm scan is performed. The scans are carried out with a step of 1 µm×2 µm. This results in a series of indentation curves. Each curve is processed according to the manufacturer's protocol with an elastic indentation model. The rigidities obtained depend on the illumination time, the shape and the spacing of the lines. They are of the order of 8.5 kPa on the rigid regions, and 3.5 kPa on the soft regions.

e) Covalent Grafting of Fibronectin on the Hydrogel

The fibronectin protein is coupled beforehand to the hetero-bifunctional crosslinker sulfo-NHS-LC-Diazirine (Sulfosuccinimidyl 6-(4,4'-azipentanamido) hexanoate, ThermoScientific Pierce; trade name: sulfo-LC-SDA), with a molar ratio of 1/480:

5 mg of fibronectin (Roche) are dissolved in 2 ml of ultrapure deionized water at 37° C. for 30 min. 1.2 mg of sulfo-LC-SDA are weighed away from light and dissolved in the fibronectin solution for 30 min at room temperature. This operation is repeated a second time, resulting in a molar ratio of 1/480. This protocol makes it possible to react the sulfo-NHS function of the sulfo-LC-SDA with the amine groups of the fibronectin while limiting the hydrolysis of the sulfo-LC-SDA. The compound so formed is a fibronectin molecule coupled to a photosensitive diazirine function. The compound formed is dialyzed through a 6-8000 membrane in a dark room and at 4° C. against 2 L of PBS+/+1× for 48 h with a change of PBS after 24 h. It is then aliquoted in small volumes (25 and 50 µL) and stored frozen at −20° C.

The hydrogel prepared according to the above protocol is dehydrated in a vertical laminar flow hood (Aura) at 26° C. overnight (dehydration of the hydrogel in the absence of fibronectin) until a dry gel is obtained. The gel therefore has a solvent content $t_a$ less than the solvent content $T_C$ of the gel at its critical evaporation time $T_c$.

In a room with UV-free lighting, 800 µL of conjugated fibronectin solution according to the above protocol is prepared at a concentration of 2.2 µg/mL in sterile deionized water, and is deposited using a pipette on the gel. The protein solution is left to incubate for 60 min at 26° C. under the laminar flow hood. The residual solution is then delicately aspirated using a pipette, and the gel is immediately illuminated by the ElecoUVP281 UV lamp for 5 min. It is then gently rinsed 3 times with a solution of PBS+/+. The functionalized gel is stored hydrated in a solution of PBS+/+ at 4° C.

f) Characterization of the Distribution of Grafted Proteins

The PBS+/+ solution is aspirated from the gel, and replaced by a saturation solution consisting of a solution of PBS+/+1×-Tween20 0.1%-BSA 2%, for 30 min with slow stirring at room temperature (20° C.). The saturation solution is aspirated using a pipette and replaced by a solution of 3 µL of primary polyclonal anti fibronectin antibody produced in rabbits (Sigma-Aldrich, F3648) diluted in 1.2 mL of PBS+/+1×-Tween20 0.1%-BSA 2%. The antibody is incubated for 1 hour with slow stirring at room temperature. It is then revealed with 1.2 mL of a solution containing 0.6 µL of a secondary antibody coupled to Alexa Fluor 488 produced in donkeys and directed against the rabbit (Molecular Probes, A21206), supplemented with a solution of PBS+/+1×-Tween20 0.1%-BSA 2% for 1 hour with slow stirring at room temperature and protected from light. The solution is then removed by aspiration and the gel is rinsed 3 times with 1.2 ml of PBS+/+1×-Tween20 0.1%-BSA 2%. The gel is then stored in a solution of PBS+/+1× at 4° C. and protected from light.

The characterization of the distribution of the grafted proteins is carried out by confocal fluorescence microscopy (Leica SP microscope). An image stack is acquired for the wavelength 488 nm with an image spacing of 0.28 µm. The stack of images is then assembled with ImageJ software and sections are extracted. The intensity profile so plotted represents the sum of the intensities over the thickness of the cell, at each point on the surface of the gel. The fluorescence intensity profile of the bottom section shows a protein distribution independent of the rigidity/porosity profile (FIG. 5).

Comparative Example 2: method in which the proteins are deposited on a hydrated Gel ($t_a > t_c$), but the method without a dehydration step once the protein has been deposited: obtaining a uniform distribution of proteins.

In this example, the hydrogel is used partially hydrated, and the binding of the protein by UV illumination is performed while the gel surface is still wet ($t_a > t_c$).

Here is transferred the pattern shown in FIG. 4 by the reference b.

a) Preparation of Basal Glass Slides

Same as Comparative Example 1.a.

b) Preparation of the Gray Level Mask

Here is transferred the pattern shown in FIG. 4 by the reference "b".

Same as Comparative Example 1. b, with a chromium deposit of 14 nm.

c) Preparation of the Hydrogel

Same as Comparative Example 1.c

Here, the assembly (mask, solution, slide) is illuminated using an Eleco UVP281 fiber optic lamp (2 W/cm$^2$) for 12 s.

d) Characterization of the Rigidity of the Hydrogel

Same as Comparative Example 1 d. A 100 μm×60 μm scan is performed. The scans are carried out with a step of 3.3 μm. The rigidities measured are of the order of 25 kPa on the patterns, and 3 kPa on the soft continuous matrix. The patterns are rigid triangular (25 kPa) of 80×40 μm, of period 200 μm, in a soft continuous matrix (3 kPa).

e) Covalent Grafting of Fibronectin on the Hydrogel

Preparation of the protein same as comparative Example 1.e.

The water covering the hydrogel prepared according to the protocol is gently aspirated using a pipette. The hydrogel is left to dehydrate in a laminar flow hood (Aura) at 26° C. for 10 min, so that its solvent content $t_a$ is greater than the solvent content $t_c$ at its critical evaporation time $T_c(t_a > t_c)$.

In a room without UV light, 800 μL of fibronectine conjugated according to the above protocol adjusted to a concentration of 2.2 μg/mL in sterile deionized water is deposited on the gel using a pipette. The protein solution is left to incubate overnight at 26° C. under the closed and turned off laminar flow hood, thus allowing time for the proteins to approach the gel without the surface drying out during this time (no dehydration).

The residual solution is then delicately aspirated using a pipette, and the gel is immediately illuminated by the ElecoUVP281 UV lamp for 5 min. It is then gently rinsed 3 times with a solution of PBS+/+. The functionalized gel is stored hydrated in a solution of PBS+/+, at 4° C.

f) Characterization of the Distribution of Grafted Proteins

Same as Comparative Example 1 f.

The fluorescence intensity profile shows a uniform distribution of proteins (FIG. 6).

Example 1 and Example 2 show that the final distribution of the nano-objects is not dependent on the rate of swelling that the hydrogel underwent during the deposition of the nano-objects (dry hydrogel in Comparative Example 1 and hydrated in Comparative Example 2). They also show that this distribution is not dependent on the time of contact between the nano-objects and the surface of the hydrogel (incubation for 66 min at 26° C. in Comparative Example 1, overnight at 26° C. in Comparative Example 2).

Example 3: Method according to the invention—modulation of the surface density of proteins on more rigid patterns of micrometric sizes Here is transferred the pattern represented in FIG. 4 by the reference "c".

a) Preparation of Basal Glass Slides

Same as Comparative Example 1.

b) Preparation of the Gray Level Mask

Same as Comparative Example 2 b.

c) Preparation of the Hydrogel

Same as Comparative Example 2 c.

d) Characterization of the Rigidity of the Hydrogel

Same as Comparative Example 2 d. Here, the rigidity of the least porous pattern is about 10 kPa, while the continuous matrix surrounding these patterns is more porous and has a rigidity of the order of 3 kPa. The surface of the hydrogel presents an alternation of hard triangular patterns (10 kPa) of 20×100 μm spaced 100 μm apart in a softer continuous matrix (3 kPa).

e) Covalent Grafting of Fibronectin on the Hydrogel

Preparation of the protein same as comparative Example 1.

The water covering the hydrogel prepared according to the above protocol is delicately aspirated using a pipette (step b2)).

The hydrogel is left to dehydrate in a laminar flow hood (Aura) at 26° C. for 1 hour (step a0')).

In a room without UV light, 800 μL of conjugated fibronectin solution according to the above protocol adjusted to a concentration of 30.6 μg/mL in sterile deionized water is deposited on the gel using a pipette. (step b). The protein solution is left to incubate for 60 min under the laminar flow hood (step b1)).

The residual solution is then delicately aspirated using a pipette (step b2)).

The wet gel of the protein solution is allowed to dehydrate for 15 min under the laminar flow hood (Aura) at 26° C. (step c)).

Then it is illuminated by the ElecoUVP281 UV lamp for 5 min (step d)). It is then gently rinsed 3 times with a solution of PBS+/+ (step e)). The functionalized gel is stored hydrated in PBS+/+ solution, at 4° C.

f) Characterization of the Distribution of Grafted Proteins

Same as Comparative Example 1 f.

The fluorescence intensity profile shows that the proteins are much denser on the harder/less porous patterns (FIG. 7).

Example 4: Method according to the invention—modulation of the surface density of proteins on more rigid patterns of millimeter sizes Here is transferred the pattern represented in FIG. 4 by the reference "d".

a) Preparation of Basal Glass Slides

Same as Comparative Example 1.

b) Preparation of the Gray Level Mask

An optical microscopy slide (26 mm×76 mm) is washed in a solution of hydrogen peroxide/concentrated sulfuric acid in a ratio of 1:1 for 20 minutes. A cleaved silicon wafer is attached to the left half of the slide. It is used to hide the transparent part before proceeding with the deposition. Then 1 nm of titanium and then 19 nm of chromium are deposited using an electron gun evaporator of the Plassys type. The slide is then made hydrophobic by an Optool treatment (Daikin DSX): immersion for 1 minute in Optool diluted to 1/1000 in perfluorohexane; then the slide is left for 1 hour in water vapor at 80° C.; finally it is immersed with slow stirring for 10 minutes in perfluorohexane.

c) Preparation of the Hydrogel

Same as Comparative Example 1 c. Here, the assembly (mask, solution, slide) is illuminated using an Eleco UVP281 fiber optic lamp (2 W/cm$^2$) for 36 s.

d) Characterization of the Rigidity of the Hydrogel

Same as Comparative Example 1 d. The rigidity profile is obtained by scanning the gel perpendicular to the rigidity border with a step of 5 μm over 400 μm. Each point of the profile is the average of 5 measurements spaced 20 μm apart taken parallel to the boundary. The hydrogel is composed of a hard region of 3 cm² (40 kPa) and a soft region of the same size (1 kPa).

e) Covalent Grafting of Fibronectin on the Hydrogel

Preparation of the protein as in Comparative Example 1 e.

The water covering the hydrogel prepared according to the above protocol is gently aspirated using a pipette.

The hydrogel is dehydrated in a laminar flow hood (Aura) at 26° C. overnight (step a0')).

In a room without UV light, 800 µL of conjugated fibronectin solution according to the above protocol adjusted to a concentration of 2.2 µg/mL in sterile deionized water is deposited on the gel using a pipette (step b)).

The protein solution is left to incubate for 60 min under the laminar flow hood. (step b1)) The residual solution is then delicately aspirated using a pipette (step b2)).

The wet gel of the protein solution is left to dehydrate for 60 min under the laminar flow hood (Aura) at 26° C. (step c)). Then it is illuminated by the ElecoUVP281 UV lamp for 5 min (step d)).

It is then gently rinsed 3 times with a solution of PBS+/+ (step e)). The functionalized gel is stored hydrated in a solution of PBS+/+, at 4° C.

f) Characterization of the Distribution of Grafted Proteins

Same as Comparative Example 1 f for the labeling of proteins and obtaining the intensity profile on the micrometric scale. The characterization at the millimeter scale is carried out by acquiring an image of 375×375 µm every millimeter by confocal microscopy. The 3D image is transformed into a 2D image by averaging the intensity of each pixel across the thickness of the stack of images. Then an average intensity is calculated from the 2D image.

The fluorescence intensity profile shows that the surface concentration of proteins is greater in the hard region (FIG. 8).

Example 5: Method according to the invention—modulation of the surface density of gold nanoparticles on more rigid patterns of micrometric sizes a) Preparation of Basal Glass Slides Same as Comparative Example 1 a.

b) Preparation of the Gray Level Mask

Same as Comparative Example 2 b. The patterns chosen are right triangles of size 40 µm×80 µm spaced 200 µm apart, from the patterns represented in FIG. 4 "b".

c) Preparation of the Hydrogel

Same as Comparative Example 2 c.

d) Characterization of the Rigidity of the Hydrogel

Same as Comparative Example 2 d.

e) Adsorption of Gold Nanoparticles

The hydrogel prepared according to the above protocol is dehydrated in a vertical laminar flow hood (Aura Mini) at 26° C. for 60 min (step a0')).

In a room without UV light, 800 µL of a solution of gold beads of 10 nm diameter (BBI Solution, reference EM GC10) diluted to 5.2×10¹² beads/mL in deionized water is deposited either for 5 min, or for 45 min on the gel surface (step b)).

The residual solution is then gently aspirated using a pipette.

The gel is left to dehydrate in a laminar flow hood at 26° C. for 4 h (step c)).

f) Characterization of the Distribution of Gold Nanoparticles

The surface density of gold nanoparticles is visualized by Scanning Electron Microscopy (SEM Zeiss Ultra Plus). The gel with the nanoparticles is covered with a metallic deposit of 3 nm of platinum (BioRad SC500 metallizer, 6.67 Pa (0.05 Torr), 16 mA, 30 s). The visualization is made at 5 keV, at a working distance of 7.5 mm for the sample having viewed the colloidal suspension 45 min, 7.6 mm for that corresponding to 5 min. Both images show a higher density of nanoparticles on the rigid pattern than the surrounding zone. The image for the 45 min sample shows quantitatively a greater number of nanoparticles on the hard and soft regions than the 5 min sample (influence incubation time).

Comparative Example 6: Increase in $T_c$ of glycerol as viscosifying agent

The solvent of the monomer solution which allows the manufacture of the hydrogel contains glycerol.

The increase in the viscosity of the solvent slows down evaporation and makes it possible to obtain a uniform surface chemistry despite a waiting time before fixation which normally induces a concentration of the nano-objects in the less porous/more rigid regions.

Here is transferred the pattern represented in FIG. 4 by the reference "b".

a) Preparation of Basal Glass Slides

Same as Comparative Example 1 a.

b) Preparation of the Gray Level Mask

Same as Comparative Example 2 b.

c) Preparation of the Hydrogel

The composition of the solution to be polymerized is as follows:

10% acrylamide (250 µl of solution initially at 40%)

0.5% N,N'-methylenebisacrylamide (Bis) (250 µl of solution initially at 2%)

0.2% Irgacure 819 w/v (Ciba, photoinitiator)

1% propylamine (initiator)

deionized water (489 µl)

0.1% glycerol (1 µL)

Then same as Comparative Example 2 c.

d) Characterization of the Rigidity of the Hydrogel

Same as Comparative Example 2 d.

The hydrogel presents rigid triangular patterns (25 kPa) of 80×40 µm, period 200 µm, in a soft continuous matrix (3 kPa).

e) Covalent Grafting of Fibronectin on the Hydrogel

Preparation of the protein same as comparative Example 1 e.

The water covering the hydrogel prepared according to the above protocol is gently aspirated using a pipette.

The hydrogel is left to dehydrate in a laminar flow hood (Aura) at 26° C. for 5 min.

In a room without UV light, 800 µL of conjugated fibronectin solution according to the above protocol adjusted to a concentration of 2.2 µg/mL in sterile deionized water is deposited on the gel using a pipette.

The protein solution is left to incubate for 60 min.

The residual solution is then gently aspirated using a pipette. The gel is dehydrated for 5 min under a laminar flow hood (Aura), then illuminated by the ElecoUVP281 UV lamp for 5 min. It is then gently rinsed 3 times with a solution of PBS+/+.

The functionalized gel is stored hydrated in a solution of PBS+/+, at 4° C.

f) Characterization of the Distribution of Grafted Proteins

Same as Comparative Example 1 f.

The fluorescence intensity profile of the bottom section shows a uniform distribution of proteins (FIG. 9).

This example 6 shows that the critical dehydration time $T_c$ may be increased by adding an adjuvant which increases the viscosity of the solvent and thus limits evaporation. In this example, uniform protein grafting is obtained despite the existence of a dehydration step after protein deposition. The duration of dehydration was not sufficient. The critical rate of dehydration has not been reached.

The invention claimed is:

1. A method of depositing nano-objects on the surface of a gel comprising a polymer matrix comprising at least two contiguous zones of distinct rigidity, said method comprising:
   a) providing a gel comprising a polymer matrix and a solvent within the polymer matrix, the polymer matrix forming a three-dimensional network capable of swelling in the presence of said solvent, wherein the solubility of the polymer matrix at 1 bar and 25° C. in the solvent is less than 1 g/L, the polymer matrix comprising at least two contiguous zones of distinct rigidity exhibiting a rigidity gradient greater than or equal to 0.1 kPa/μm, then
   b) depositing nano-objects with an average diameter of 1 to 1000 nm on the surface of the gel, then
   c) evaporating the solvent from the gel at least until a variation in a rate of evaporation of the solvent from at least one least rigid zone of the gel is not constant over time, by which the nano-objects migrate towards at least one more rigid zone of the gel and a gel is obtained whose surface is at least partially coated with the nano-objects, and where the surface density of the nano-objects of the at least one most rigid zone among the at least two contiguous zones is greater to that of the at least one least rigid zone among the at least two contiguous zones, wherein evaporation of the solvent comprises at least two periods, a first evaporation period and a second evaporation period;
   wherein during the first evaporation period, solvent is continuously removed from the gel surface by capillary forces and the solvent content decreases at a constant rate;
   wherein during the second evaporation period, the diffusion forces become predominant over the capillary forces and the removal of the solvent from the gel is controlled by the diffusion of the solvent into the pores of the gel towards its surface;
   wherein during c), the evaporation rate reaches a critical evaporation rate at a critical evaporation time Tc, which marks the transition between the first and the second evaporation periods,
   wherein said critical evaporation time Tc is not identical between the at least one most rigid zone and the at least one least rigid zone,
   wherein the polymer matrix of the gel comprises a polysiloxane;
   wherein the solvent present within the polymer matrix of the gel is selected from the group consisting of pentane, triethylamine, diisopropylamine, and xylene;
   wherein the nano-objects are not cells; and
   wherein when the nano-objects are proteins and/or peptides and/or polysaccharides, and
   wherein the method further comprises:
   d) covalent grafting of the proteins and/or the peptides and/or the polysaccharides on the gel.

2. The method according to claim 1, wherein the solvent comprises a viscosifying agent.

3. The method according to claim 1, wherein the nano-objects are the polysaccharides, the proteins and the peptides.

4. The method according to claim 1, wherein the nano-objects are the proteins inducing cell adhesion via integrins and the peptides inducing cell adhesion via integrins.

5. The method according to claim 1, wherein the nano-objects are fibronectin, collagen, laminin, and RGD-type peptides.

6. The method according to claim 1, wherein the polymer matrix of the gel comprises poly (dimethylsiloxane).

7. The method according to claim 1 wherein, during c), at the start of evaporation, content of inorganic salts in the solvent of the gel is less than 6 g/L.

8. A method of depositing nano-objects on the surface of a gel comprising a polymer matrix comprising at least two contiguous zones of distinct rigidity, said method comprising:
   a) providing a gel comprising a polymer matrix and a solvent within the polymer matrix, the polymer matrix forming a three-dimensional network capable of swelling in the presence of said solvent, wherein the solubility of the polymer matrix at 1 bar and 25° C. in the solvent is less than 1 g/L, the polymer matrix comprising at least two contiguous zones of distinct rigidity exhibiting a rigidity gradient greater than or equal to 0.1 kPa/μm, then
   b) depositing nano-objects with an average diameter of 1 to 1000 nm on the surface of the gel, then
   c) evaporating the solvent from the gel at least until a variation in a rate of evaporation of the solvent from at least one least rigid zone of the gel is not constant over time, by which the nano-objects migrate towards at least one more rigid zone of the gel and a gel is obtained whose surface is at least partially coated with the nano-objects, and where the surface density of the nano-objects of the at least one most rigid zone among the at least two contiguous zones is greater to that of the at least one least rigid zone among the at least two contiguous zones, wherein evaporation of the solvent comprises at least two periods, a first evaporation period and a second evaporation period;
   wherein during the first evaporation period, solvent is continuously removed from the gel surface by capillary forces and the solvent content decreases at a constant rate;
   wherein during the second evaporation period, the diffusion forces become predominant over the capillary forces and the removal of the solvent from the gel is controlled by the diffusion of the solvent into the pores of the gel towards its surface;
   wherein during c), the evaporation rate reaches a critical evaporation rate at a critical evaporation time Tc, which marks the transition between the first and the second evaporation periods,
   wherein said critical evaporation time Tc is not identical between the at least one most rigid zone and the at least one least rigid zone,
   wherein the polymer matrix of the gel comprises a polyacrylamide, said polyacrylamide being obtained from the polymerization of acrylamide and N,N'-methylenebisacrylamide;
   wherein the solvent present within the polymer matrix of the gel is an aqueous solution;
   wherein the nano-objects are not cells; and
   wherein when the nano-objects are proteins and/or peptides and/or polysaccharides, and
   wherein the method further comprises:
   d) covalent grafting of the proteins and/or the peptides and/or the polysaccharides on the gel.

9. The method according to claim 8 wherein, during c), at the start of evaporation, content of inorganic salts in the solvent of the gel is less than 6 g/L.

* * * * *